US012591705B2

(12) United States Patent
Gutta et al.

(10) Patent No.: US 12,591,705 B2
(45) Date of Patent: *Mar. 31, 2026

(54) STANDARD COMPLIANT DATA COLLECTION DURING A COMMUNICATION SESSION

(71) Applicant: Twilio Inc., San Francisco, CA (US)

(72) Inventors: Krishnaprasad Gutta, San Francisco, CA (US); Christer Jan Erik Fahlgren, San Francisco, CA (US)

(73) Assignee: Twilio Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,908

(22) Filed: Jan. 26, 2023

(65) Prior Publication Data

US 2023/0169207 A1 Jun. 1, 2023

Related U.S. Application Data

(63) Continuation of application No. 16/885,684, filed on May 28, 2020, now Pat. No. 11,604,892.

(Continued)

(51) Int. Cl.
G06Q 20/38 (2012.01)
G06F 21/62 (2013.01)
G16H 10/60 (2018.01)

(52) U.S. Cl.
CPC ....... G06F 21/6245 (2013.01); G06Q 20/382 (2013.01); G06Q 20/383 (2013.01); G16H 10/60 (2018.01); G06F 21/6254 (2013.01)

(58) Field of Classification Search
CPC ...... G06F 21/00–88; G06Q 20/00–425; G16H 10/00–65
See application file for complete search history.

(56) References Cited

U.S. PATENT DOCUMENTS 8,949,969 B2 * 2/2015 Newman .............. G06Q 20/405
726/15
9,003,049 B1 * 4/2015 Simoes ............... H04L 65/1104
709/230

(Continued)

OTHER PUBLICATIONS

Bonner et al., Implementing the Payment Card Industry (PCI) Data Security Standard (DSS), Telkomnika, Aug. 2011 (Year: 2011).*

(Continued)

*Primary Examiner* — Chenyuh Kuo
(74) *Attorney, Agent, or Firm* — Schwegman Lundberg & Woessner, P.A.

(57) ABSTRACT

Disclosed are systems, methods, and non-transitory computer-readable media for standard compliant collection of sensitive data during a communication session. A standard compliant data collection system is used to provide the standard compliant collection of sensitive data. For example, in response to receiving an indication that a user is to provide sensitive data during an active communication session between the user and an agent, a standard compliant data collection mode is invoked. As a result, communication within the active communication session is routed between the user and the standard compliant data collection system via a secure connection, during which sensitive data is collected in a standard compliant manner. Once collection of the user's sensitive data has been completed, the standard compliant data collection mode is ended, and communication within the active communication session is routed between the user and the agent.

20 Claims, 8 Drawing Sheets

Related U.S. Application Data

(60) Provisional application No. 62/853,502, filed on May 28, 2019.

(56) References Cited

U.S. PATENT DOCUMENTS

| | | | |
|---|---|---|---|
| 9,015,297 B2 | 4/2015 | Putman et al. | |
| 9,420,020 B2 * | 8/2016 | Madan | H04L 65/4015 |
| 10,447,797 B2 | 10/2019 | Dingwall et al. | |
| 10,447,860 B1 * | 10/2019 | Hartman | H04M 7/006 |
| 10,764,435 B2 * | 9/2020 | Deole | H04M 7/0057 |
| 11,063,943 B2 | 7/2021 | Stoops et al. | |
| 11,070,487 B2 * | 7/2021 | Hoffmann | H04L 41/40 |
| 11,604,892 B2 | 3/2023 | Gutta et al. | |
| 2007/0064891 A1 * | 3/2007 | Lee | H04M 15/00 |
| | | | 379/114.15 |
| 2012/0014375 A1 * | 1/2012 | Simoes | H04M 3/428 |
| | | | 370/352 |
| 2016/0140544 A1 * | 5/2016 | Howe | G06F 21/6254 |
| | | | 705/74 |
| 2018/0084110 A1 * | 3/2018 | Fraizer | H04L 63/0421 |
| 2020/0028968 A1 * | 1/2020 | Mendiratta | H04M 3/5166 |
| 2020/0380161 A1 | 12/2020 | Gutta et al. | |

OTHER PUBLICATIONS

Rosenberg et al., Request for Comments: 5850 'A Call Control and Multi-Party Usage Framework for the Session Initiation Protocol (SIP)', Internet Engineering Task Force (IETF), May 2010 (Year: 2010).*

"U.S. Appl. No. 16/885,684, Non Final Office Action mailed May 31, 2022", 13 pgs.

"U.S. Appl. No. 16/885,684, Response filed Aug. 31, 2022 to Non Final Office Action mailed May 31, 2022", 11 pgs.

"U.S. Appl. No. 16/885,684, Examiner Interview Summary mailed Oct. 6, 2022", 2 pgs.

"U.S. Appl. No. 16/885,684, Notice of Allowance mailed Oct. 20, 2022", 20 pgs.

Bonner, Enda, "Implementing the Payment Card Industry (PCI) Data Security Standard (DSS)", Telkomnika, vol. 9, No. 2, (Year: 2011), (Aug. 2011), 13 pgs.

Rosenberg, J, "A Call Control and Multi-Party Usage Framework for the Session Initiation Protocol (SIP)", Request for Comments: 5850' Internet Engineering Task Force (IETF), (Year: 2010), (May 2010), 44 pgs.

* cited by examiner

100

CLIENT DEVICE 104

CLOUD-BASED COMMUNICATION PLATFORM 108

STANDARD COMPLIANT DATA COLLECTION SYSTEM 110

COMMUNICATION NETWORK 114

CLIENT DEVICE 102

ONLINE SERVICE 106

DATA ANONYMIZATON SYSTEM 112

STANDARD COMPLIANT DATA COLLECTION
SYSTEM
110

API COMMAND RECEIVING MODULE
202

SECURE CONNECTION CREATION MODULE
204

STANDARD COMPLIANT DATA COLLECTION
MODULE
206

STANDARD COMPLIANT DATA STORAGE
MODULE
208

TERMINATION MODULE
210

DATA STORAGE
212

500

START

RECEIVE AN INDICATION THAT A USER ENGAGED IN A COMMUNICATION SESSION HAS BEEN PROMPTED TO PROVIDE SENSITIVE DATA
502

INVOKE A STANDARD COMPLIANT DATA COLLECTION MODE OF THE COMMUNICATION SESSION
504

DETERMINE THAT THE USER HAS COMPLETED PROVIDING THE SENSITIVE DATA
506

END THE STANDARD COMPLIAND DATA COLLECTION MODE
508

END

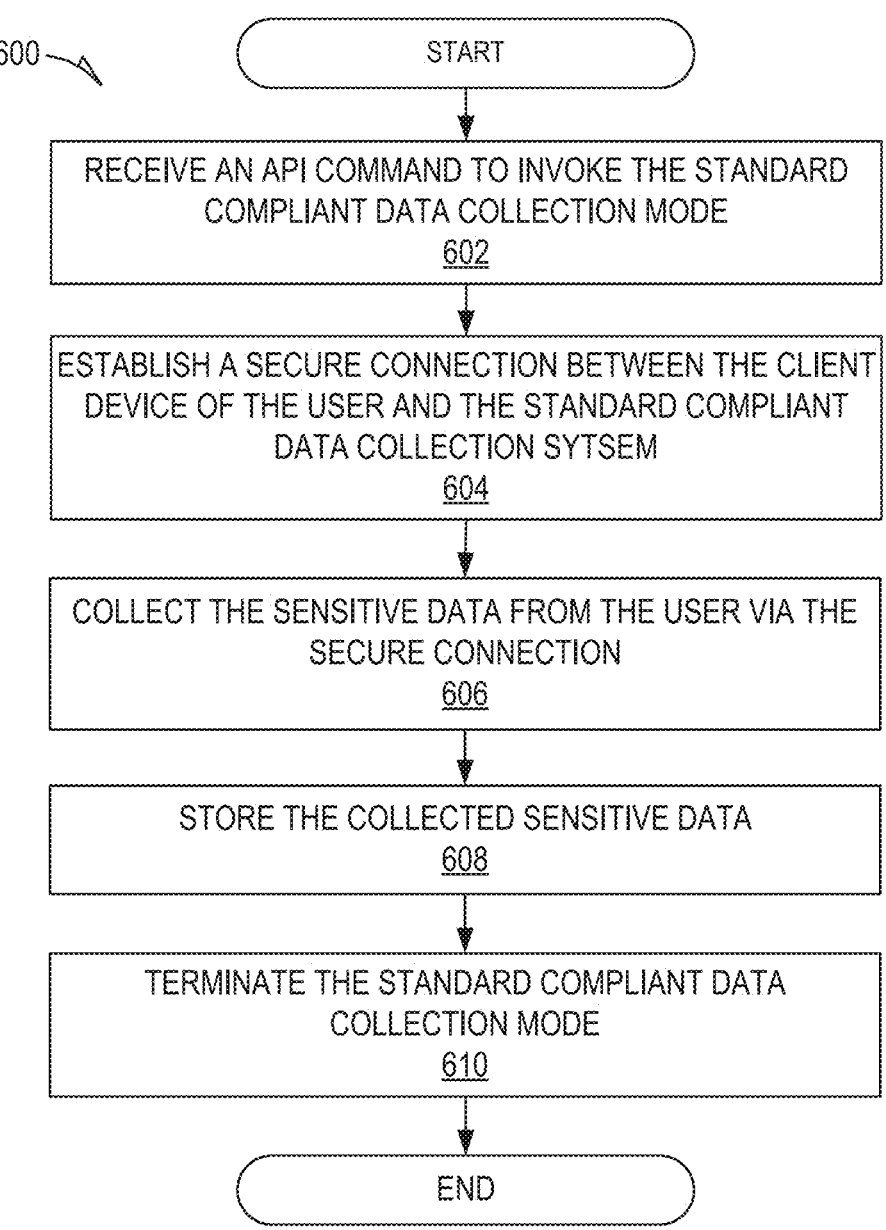

600

START

RECEIVE AN API COMMAND TO INVOKE THE STANDARD
COMPLIANT DATA COLLECTION MODE
602

ESTABLISH A SECURE CONNECTION BETWEEN THE CLIENT
DEVICE OF THE USER AND THE STANDARD COMPLIANT
DATA COLLECTION SYTSEM
604

COLLECT THE SENSITIVE DATA FROM THE USER VIA THE
SECURE CONNECTION
606

STORE THE COLLECTED SENSITIVE DATA
608

TERMINATE THE STANDARD COMPLIANT DATA
COLLECTION MODE
610

END

*FIG. 6*

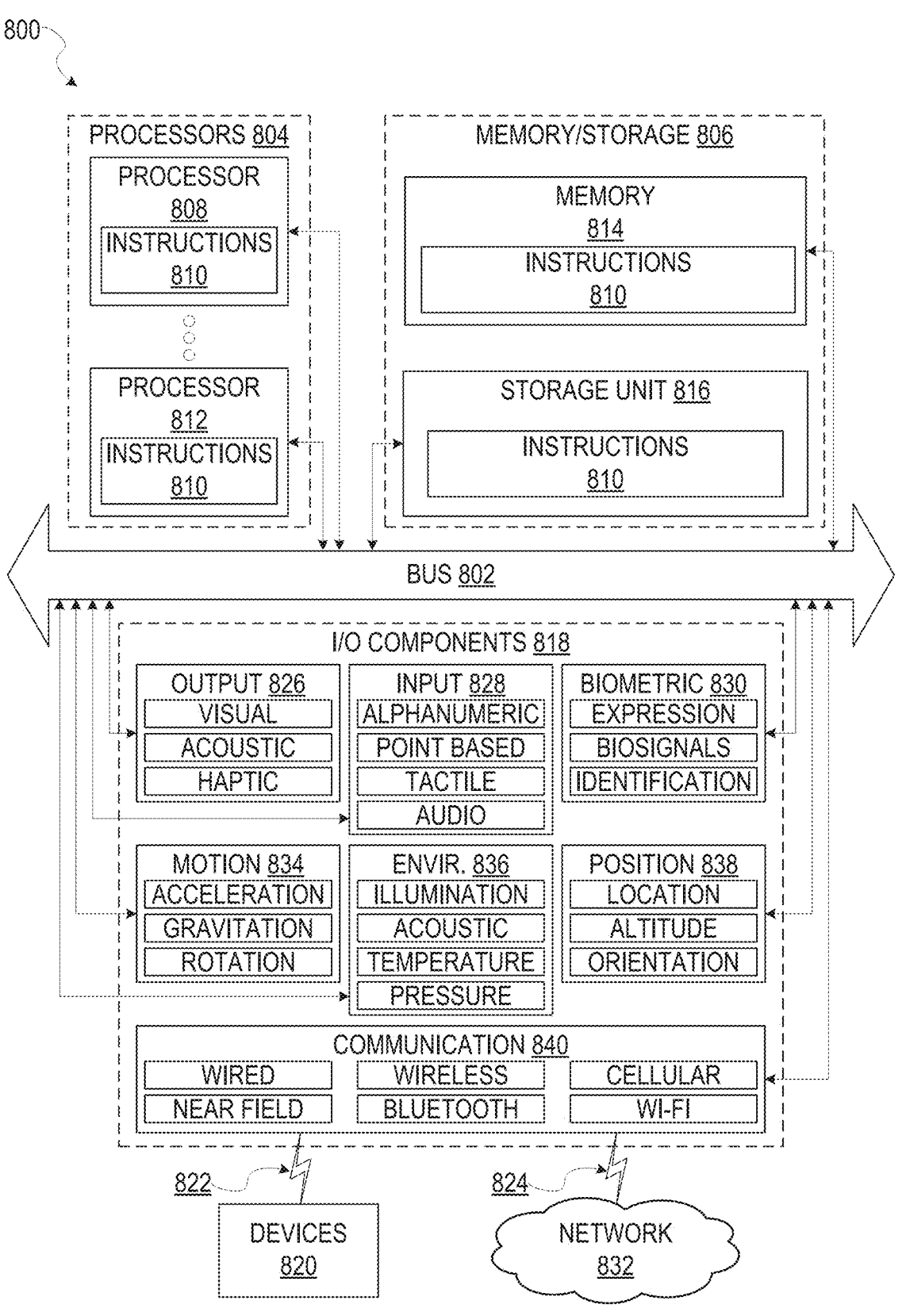

800

PROCESSORS 804

PROCESSOR
808

INSTRUCTIONS
810

PROCESSOR
812

INSTRUCTIONS
810

MEMORY/STORAGE 806

MEMORY
814

INSTRUCTIONS
810

STORAGE UNIT 816

INSTRUCTIONS
810

BUS 802

I/O COMPONENTS 818

| OUTPUT 826 | INPUT 828 | BIOMETRIC 830 |
|---|---|---|
| VISUAL | ALPHANUMERIC | EXPRESSION |
| ACOUSTIC | POINT BASED | BIOSIGNALS |
| HAPTIC | TACTILE | IDENTIFICATION |
| | AUDIO | |

| MOTION 834 | ENVIR. 836 | POSITION 838 |
|---|---|---|
| ACCELERATION | ILLUMINATION | LOCATION |
| GRAVITATION | ACOUSTIC | ALTITUDE |
| ROTATION | TEMPERATURE | ORIENTATION |
| | PRESSURE | |

COMMUNICATION 840

| WIRED | WIRELESS | CELLULAR |
|---|---|---|
| NEAR FIELD | BLUETOOTH | WI-FI |

822

DEVICES
820

824

NETWORK
832

*FIG. 8*

STANDARD COMPLIANT DATA COLLECTION DURING A COMMUNICATION SESSION

CROSS-REFERENCE TO RELATED APPLICATIONS

The present application claims the benefit of priority of U.S. application Ser. No. 16/885,684, filed May 28, 2020, which claims the benefit of priority of U.S. Provisional Application No. 62/853,502, filed on May 28, 2019, each of which is incorporated herein by reference in its entirety.

TECHNICAL FIELD

An embodiment of the present subject matter relates generally to communication sessions and, more specifically, to standard compliant data collection.

BACKGROUND

Communications have transformed rapidly in the past ten years. In addition to traditional communication channels, a variety of newly adopted communication channels are now routinely used to conduct business. For example, contact center agents often use direct message conversations, phone calls, in-app messaging, and text conversations to communicate with customers. In some instances, a customer may be asked to provide sensitive data, including their credit card information, social security number, patient history, etc., during a communication session (e.g., call, chat, etc.) with an agent. To protect each user's sensitive data, industry standards have been put in place to ensure that entities collecting sensitive data meet minimum levels of security when they store, process, and/or transmit the sensitive data. However, implementing systems to comply with industry standards can be difficult, particularly for smaller businesses that have insufficient resources and technical knowledge and/or when multiple communication channels are used to collect the sensitive data. Accordingly, improvements are needed.

SUMMARY

Certain industries such as the Payment Card Industry (PCI), mandate that a set of standards be followed when collecting, storing, processing, and/or transmitting sensitive data (e.g., credit card data, medical patient data, etc.). Implementing systems that comply with these standards may be difficult, particularly for smaller entities with limited resources and/or when multiple communication channels are used to collect sensitive data. A cloud based standard compliant data collection system simplifies this process by providing standard compliant data collection as a cloud-based service that multiple entities (e.g., companies, online services, etc.) can use to provide standard compliant data collection.

The standard compliant data collection system provides an Application Programming Interface (API), which enables entities to use the functionality of the standard compliant data collection system to provide standard compliant data collection in relation to their provided services. For example, an entity needing to gather sensitive data from a customer during a communication session may use an API to communicate with the standard compliant data collection system to provide standard compliant data collection in relation to the communication session, as well as subsequent storage, processing and/or transmitting of the collected sensitive data in a standard compliant manner.

A communication session is any type of communication between two or more client devices transmitted as part of a conversation between users of the client devices. For example, a communication session may include text communication (e.g., SMS, MIMS, IP messaging), voice communication (e.g., phone call), video communication (e.g., video conference), etc., transmitted between client devices. To provide for standard compliant data collection during a communication session, an entity uses the API provided by the standard compliant data collection system to invoke a standard compliant data collection mode in relation to the communication session. The API may allow the entity to customize performance of the standard compliant data collection system, such as by defining a message flow, language, failure handling, and the like.

Invoking the standard compliant data collection mode causes communication within the communication session to be temporarily routed between the standard compliant data collection system and the client device of the user providing the sensitive data. For example, the standard compliant data collection system establishes a secure connection between the client device of the user and the standard compliant data collection system, which is used to collect the user's sensitive data in a standard compliant manner. During the standard compliant data collection mode, an agent or other user that was engaged in the communication session with the user providing the sensitive data is placed on a hold and/or the initial communication session is terminates. As a result, the agent cannot receive communications transmitted by the client device of the user providing the sensitive data during the standard compliant data collection mode.

Once the user has successfully provided their sensitive data, the standard compliant data collection mode is ended. As a result, the secure connection between the client device of the user and the standard compliant data collection system is terminated and communication within the communication session is again routed between the client devices of the agent and the user. For example, the hold placed on the agent may be ended and/or a new communication session may be established between the user and agent.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which:

FIG. 6 is a flowchart showing an example method of invoking a standard compliant data collection mode, according to some example embodiments.

FIG. 8 is a block diagram illustrating components of a machine, according to some example embodiments, able to read instructions from a machine-readable medium (e.g., a machine-readable storage medium) and perform any one or more of the methodologies discussed herein.

DETAILED DESCRIPTION

In the following description, for purposes of explanation, various details are set forth in order to provide a thorough understanding of some example embodiments. It will be apparent, however, to one skilled in the art, that the present subject matter may be practiced without these specific details, or with slight alterations.

Reference in the specification to "one embodiment" or "an embodiment" means that a particular feature, structure, or characteristic described in connection with the embodiment is included in at least one embodiment of the present subject matter. Thus, the appearances of the phrase "in one embodiment" or "in an embodiment" appearing in various places throughout the specification are not necessarily all referring to the same embodiment.

For purposes of explanation, specific configurations and details are set forth in order to provide a thorough understanding of the present subject matter. However, it will be apparent to one of ordinary skill in the art that embodiments of the subject matter described may be practiced without the specific details presented herein, or in various combinations, as described herein. Furthermore, well-known features may be omitted or simplified in order not to obscure the described embodiments. Various examples may be given throughout this description. These are merely descriptions of specific embodiments. The scope or meaning of the claims is not limited to the examples given.

Figure 1:
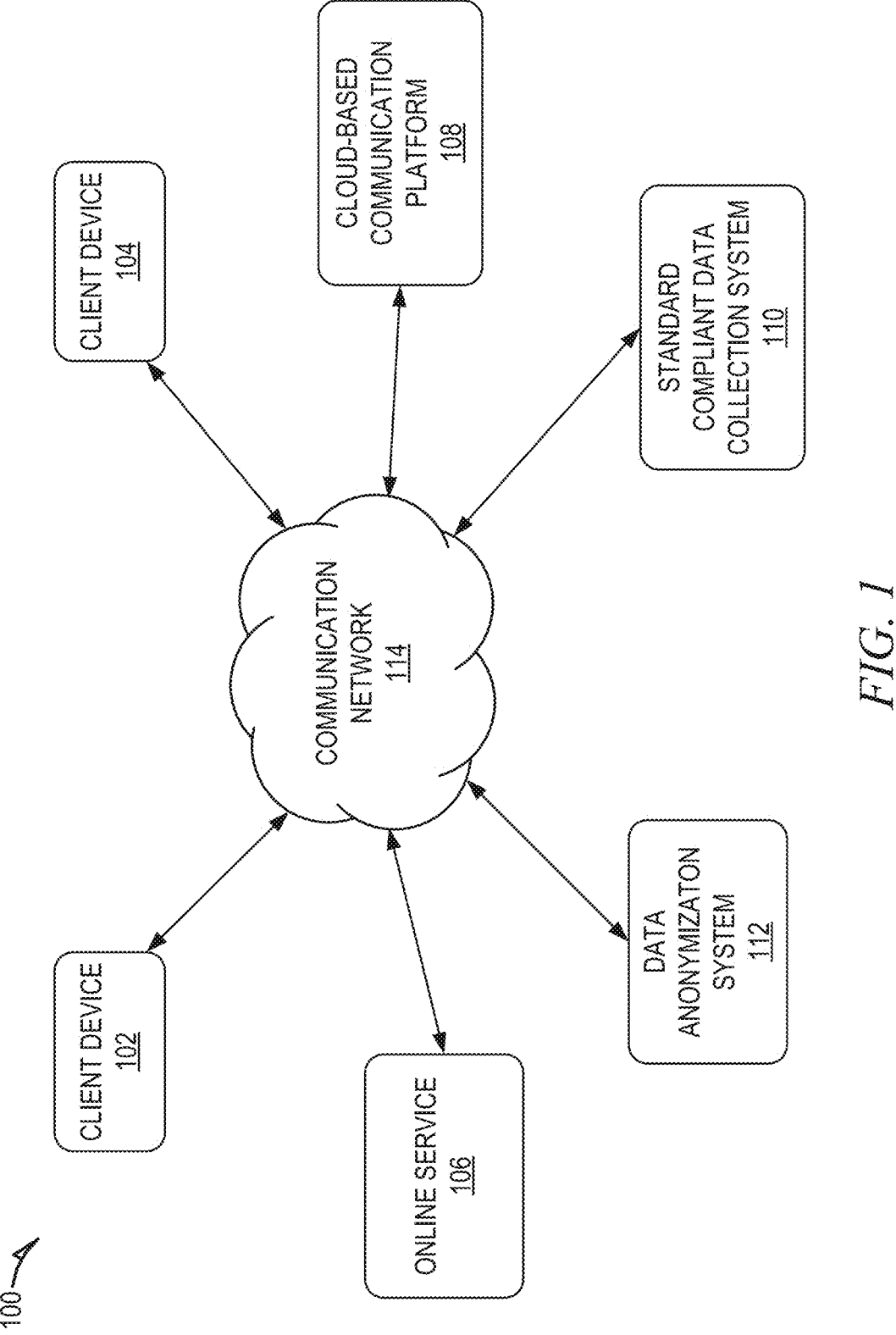
FIG. 1 shows an example system for providing standard compliant data collection during communication sessions, according to some example embodiments.

Disclosed are systems, methods, and non-transitory computer-readable media for standard compliant data collection during a communication session. FIG. 1 shows an example system 100 for providing standard compliant data collection during communication sessions, according to some example embodiments. As shown, multiple devices (i.e., client device 102, client device 104, online service 106, cloud-based communication platform 108, standard compliant data collection system 110, and data anonymization system 112) are connected to a communication network 114 and configured to communicate with each other through the use of the communication network 114. The communication network 114 is any type of network, including a local area network ("LAN"), such as an intranet, a wide area network ("WAN"), such as the internet, or any combination thereof. Further, the communication network 114 may be a public network, a private network, or a combination thereof. The communication network 114 is implemented using any number of communications links associated with one or more service providers, including one or more wired communication links, one or more wireless communication links, or any combination thereof. Additionally, the communication network 114 is configured to support the transmission of data formatted using any number of protocols.

Multiple computing devices can be connected to the communication network 114. A computing device is any type of general computing device capable of network communication with other computing devices. For example, a computing device can be a personal computing device such as a desktop or workstation, a business server, or a portable computing device, such as a laptop, smart phone, or a tablet PC. A computing device can include some or all of the features, components, and peripherals of the machine 800 shown in FIG. 8.

To facilitate communication with other computing devices, a computing device includes a communication interface configured to receive a communication, such as a request, data, etc., from another computing device in network communication with the computing device and pass the communication along to an appropriate component running on the computing device. The communication interface also sends a communication to another computing device in network communication with the computing device.

In the system 100, users interact with an online service 106 to utilize functionality provided by the online service 106. For example, users use the client devices 102 and 104 that are connected to the communication network 114 by direct and/or indirect communication to communicate with and utilize the functionality of the online service 106. The online service 106 may be any type of service provided online, such as a ride-sharing service, reservation service, retail service, news service, etc.

Although the shown system 100 includes only two client devices 102, 104, one online service 106 and one cloud-based communication platform 108, this is not meant to be limiting. One skilled in the art would appreciate that the system 100 can include any number of client devices 102, 104, online services 106 and/or cloud-based communication platforms 108. Further, an online service 106 and/or cloud-based communication platform 108 may concurrently accept connections from and interact with any number of client devices 102, 104, as well as support connections from a variety of different types of client devices 102, 104, such as desktop computers; mobile computers; mobile communications devices, e.g. mobile phones, smart phones, tablets; smart televisions; set-top boxes; and/or any other network enabled computing devices. Hence, the client devices 102 and 104 may be of varying type, capabilities, operating systems, etc.

A user interacts with the online service 106 via a client-side application installed on the client devices 102 and 104. In some embodiments, the client-side application includes an online service 106 specific component. For example, the component may be a stand-alone application, one or more application plug-ins, and/or a browser extension. However, the users may also interact with the online service 106 via a third-party application, such as a web browser, that resides on the client devices 102 and 104 and is configured to communicate with the online service 106. In either case, the client-side application presents a user interface (UI) for the user to interact with the online service 106. For example, the user interacts with the online service 106 via a client-side application integrated with the file system or via a webpage displayed using a web browser application.

The online service 106 is one or more computing devices configured to provide any type of online service, such as a banking service, travel service, retail service, health care service, etc. As a part of its provided functionality, the online service 106 may enable users of the online service 106 to communicate with agents of the online service 106. That is, the online service 106 may enable users to initiate communication sessions with agents of the online service in which the participants of the communication session may communicate with each other via voice, text, video, etc. For example, a banking service may allow a user to initiate a communication session with an agent to discuss banking issues, check account balances, transfer funds, etc. Likewise, a retail service may allow users to initiate a communication session with an agent to place an order, initiate a return, etc.

A communication session is any type of communication between two or more client devices 102, 104, such as text communication, voice communication (e.g., phone call), video communication (e.g., video conference), etc. Implementing communication functionality may be difficult, particularly for an online service 106 that provides services unrelated to communications, such as banking services, health care services, retail services, etc. The cloud-based communication platform 108 alleviates these issues by providing cloud-based communication functionality that can be implemented by an online service 106 to provide communication services as part of the services provided by the online service 106. Accordingly, the cloud-based communication platform 108 is a SaaS provider that concurrently provides communication services for multiple online services 106.

To utilize the communication services provided by the cloud-based communication platform 108, an online service 106 creates an account with the cloud-based communication platform 108 and uses an API provide by the cloud-based communication platform 108 to modify a programming application and/or website of the online service 106. Inclusion of the API causes the programming application and/or website to communicate with the cloud-based communication platform 108 to provide communication services provided by the cloud-based communication platform 108 through the application and/or website of the online service 106.

As an example, an online service 106 that provides banking services application may utilize the communication services provided by the cloud-based communication platform 108 to enable users and bank agents to communicate with each other. As another example, an online service 106 that provides health insurance services may utilize the communication services provided by the cloud-based communication platform 108 to enable patients and insurance agents to communicate with each other. To accomplish this, the online service 106 may use the API provided by the cloud-based communication platform 108 to cause the online service 106 to communicate with the cloud-based communication platform 108 to initiate a communication session between specified users. For example, the online service 106 transmits an API call to the cloud-based communication platform 108 to execute the communication session. The API provided by the cloud-based communication platform 108 may define the syntax and format for the API call, including the parameters to include in the API call to initiate the desired communication session. As another example, an online service 106 may simply publish or otherwise provide their customers with contact information, such as a phone number, for reaching their call center to be connected to an agent.

The cloud-based communication platform 108 may provide its users (e.g., online services 106 utilizing the functionality of the cloud-based communication platform 108) with standard compliant data collection services. As explained earlier, certain industries such as the Payment Card Industry (PCI), mandate that a set of standards be followed when collecting sensitive data, such as credit card data.

Implementing systems that comply with these standards may be difficult, particularly when using multiple communication channels. The standard compliant data collection system 110 alleviates these issues by providing cloud-based functionality that can be easily implemented by an online service 106 to facilitate standard compliant data collection during communication sessions.

The online service 106 utilizes the standard compliant data collection system 110 to provide standard compliant collection of sensitive data during communication sessions between users and agents of the online service 106. The online service 106 therefore does not need to develop and maintain a standard compliant system itself. In this way, standard compliant data collection system 110 is provided as a SaaS solution for standard compliant data collection.

The standard compliant data collection system 110 provides an Application Programming Interface (API), which can be leveraged by an online service 106 to offer standard compliant data collection to users of the online service 106. The online service 106 simply incorporates the API into their website, application, or other software, to utilize the functionality of the standard compliant data collection system 110 within their service. For example, the API causes an API command to be transmitted to the standard compliant data collection system 110 to initiate a standard compliant data collection mode in relation to a communication session. This provides the online service 106 with an easy way to provide standard compliant data collection functionality as part of their provided services, while also reducing the resource usage of the computing devices facilitating the online service 106.

The online service 106 uses the API provided by the standard compliant data collection system 110 to initiate a standard compliant data collection mode in relation to a communication session, such as an active communication session between a user and an agent of the online service 106. For example, the standard compliant data collection system 110 may initiate the standard compliant data collection mode in response to receiving an indication that the user is to provide sensitive data via the communication session. The indication may be any type of indicator that a user engaged in the communication session is being prompted to provide sensitive data via the communication session. For example, a user or agent may be enabled to initiate a standard compliant data collection mode by selecting a user interface element such as a button. Accordingly, selection of the user interface element would be an indication that the user is to provide sensitive data via the communication session. As another example, the online service 106 may analyze communications transmitted as part of the communication session and determine that the user is being asked to provide sensitive data.

Upon receiving an indication that the user is to provide sensitive data via the communication session, the online service 106 uses an API command to communicate with the standard compliant data collection system 110 to initiate a standard compliant data collection mode in relation to the communication session. The API command may provide data to the standard compliant data collection system 110 for use in initiating the standard compliant data collection mode, such as data identifying the communication session, the client device 102 of the user, the client device 104 of the agent, the type of sensitive data to be collected, etc. The API command may also include configuration data defining performance of the standard compliant data collection mode. For example, the API command my define a message flow language, failure handling, and the like.

The standard compliant data collection system 110 receives the API command and initiates the standard compliant data collection mode based on the configuration data included in the API command. For example, the standard compliant collection system 110 establishes a secure connection between the client device 102 of the user providing the sensitive data and the standard compliant data collection system 110. Communication within the communication session is then routed between the standard compliant data collection system 110 and the client device 102 using the secure connection. While in the standard compliant data collection mode, the user may provide their sensitive data directly to the standard compliant data collection system 110, where it is collected, stored and otherwise managed in a standard-compliant manner. During this time, the agent of the online service 106 is not a party to the communication session and therefore may not have access to the sensitive data collected by the standard compliant data collection system 110.

The standard compliant data collection system 110 may collect the user's sensitive data based on the configuration data included in the API command. The configuration data may include a set of instructions, such as a programming script, that is executed by the standard compliant data collection system 110 to collect the sensitive data. For example, the API command may dictate a message flow for collecting the user's sensitive data, such as by defining the prompts that are presented to the data, the order of the prompts, the types of data to be collected, and the like. The prompts presented to the user may be audio files, which are identified in the API command along with a specified order in which the prompts are to be presented. The standard compliant data collection system 110 may access the audio files identified in the configuration data and cause playback of the audio filed to the user in the specified order. As another example, the configuration data may include text for the prompts to be presented to the user. In this type of embodiment, the standard compliant data collection system 110 converts the text to audio, which is then played for the user.

The standard compliant data collection system 110 may also use a language specified by the configuration data. For example, the configuration data may define a language based on a known spoken language or nationality of the user. As another example, the configuration data may define a language based on a geographic location of the user. The standard compliant data collection system 110 may gather an appropriate version of an audio file based on the identified language and/or convert the included text to audio based on the specified language.

The configuration data may also define error handling during the standard compliant data collection mode. For example, the configuration data may identify specified action to be performed in the event of an error, such as causing a prompt to be played to the user, causing a notification to be transmitted to a specified destination, and the like. In some embodiments, the configuration data may include a resource identifier, such as a Uniform Resource Identifier (URI), that identifies the specified destination and can be used to initiate a notification when an error occurs. The standard compliant data collection system 110 may embed state information into the URI based on the communication session and/or the detected error, which is then transmitted to the specified destination.

The configuration data may also define performance of other reporting and notifications. For example, the configuration data may define event triggers that cause a notification to be sent to a specified destination. The event trigger may be any type of even, such as the user's sensitive data being successfully collected. The configuration data may include resource identifiers associated with the event triggers for transmitting the corresponding notifications, as well define the data to be included in the notification. The standard compliant data collection system 110 may embed the specified data into the URI, which is then transmitted to the specified destination.

Once the user has successfully provided their sensitive data, the standard compliant data collection mode is ended by the standard compliant data collection system 110. That is, the standard compliant data collection system 110 terminates the secure connection between the client device 102 of the user and the standard compliant data collection system 110. Routing of communications within the communication session is then reestablished between the agent of the online service 106 and the user.

Although the standard compliant data collection system 110 is shown separately from the cloud-based communication platform 108, this is not meant to be limiting. In some embodiments, the functionality of the standard compliant data collection system 110 is partially or completely integrated within the cloud-based communication platform 108. Accordingly, communications described as being transmitted to/from the standard compliant data collection system 110 may be transmitted to the cloud-based communication platform 108.

In some embodiments, an online service 106 may wish to maintain a record of communication sessions with agents, including portions of the communication session in which the user is providing sensitive data. For example, the online service 106 may wish to record the communication session for training purposes or to provide an agent with live feedback that the user has provided their sensitive data. The data anonymization system 112 allows an online service 106 to maintain a record of the complete communication session while also protecting the sensitive data of the user. The data anonymization system 112 accomplishes this by modifying data transmitted as part of the communication session to replace sensitive data with default replacements. For example, credit card numbers entered during a chat session may be replaced with default symbols, such as the star (i.e., *) symbol. As another example, phone tones indicating numbers entered by a user may be replaced with a default tone that does not correspond to a number of a key. As a result, an agent is made aware that the user has entered a number but cannot discern what number was entered.

Figure 2:
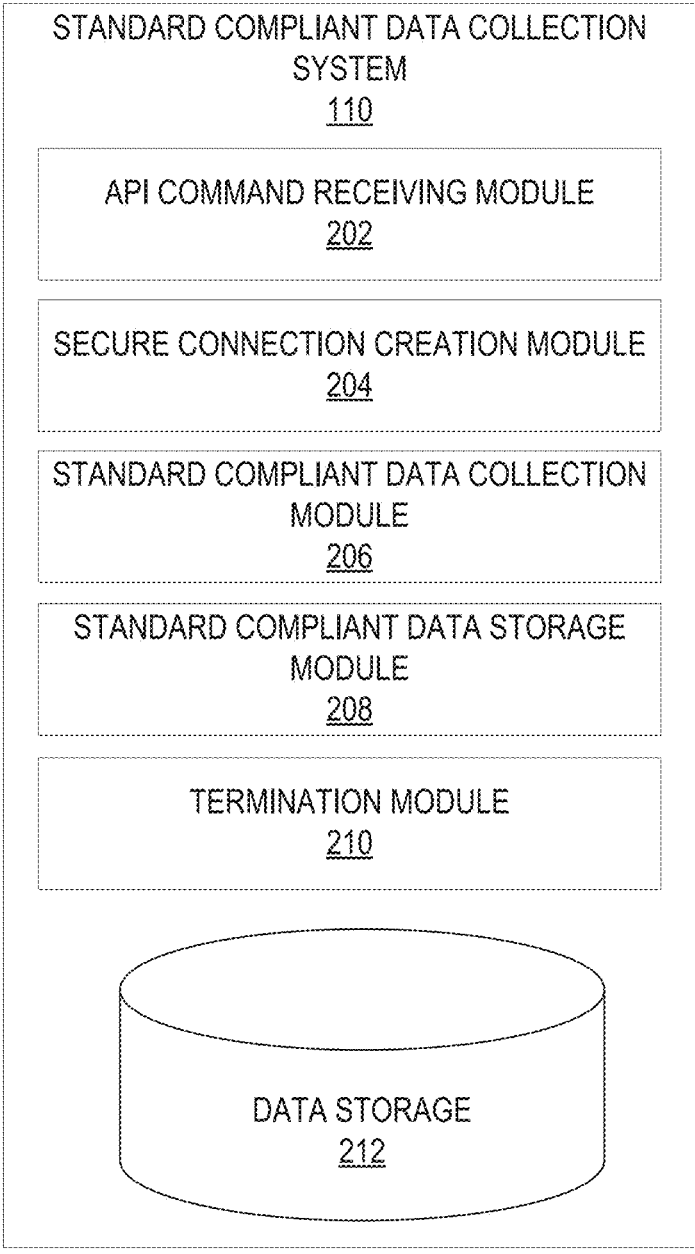
FIG. 2 is a block diagram of the standard compliant data collection system, according to some example embodiments.

FIG. 2 is a block diagram of the standard compliant data collection system 110, according to some example embodiments. To avoid obscuring the inventive subject matter with unnecessary detail, various functional components (e.g., components) that are not germane to conveying an understanding of the inventive subject matter have been omitted from FIG. 2. However, a skilled artisan will readily recognize that various additional functional components may be supported by the standard compliant data collection system 110 to facilitate additional functionality that is not specifically described herein. Furthermore, the various functional components depicted in FIG. 2 may reside on a single computing device or may be distributed across several computing devices in various arrangements such as those used in cloud-based architectures.

As shown, the standard compliant data collection system 110 includes an API command receiving module 202, a secure connection creation module 204, a standard compliant data collection module 206, a standard compliant data storage module 208, a termination module 210, and a data storage 212.

The API command receiving module 202 receives an API command to initiate a standard compliant data collection mode for an active communication session. The API command may be received from a client device 102 of a user, client device 104 of an agent, the cloud-based communication platform 108 or the online service 106. The API command may include data used to initiate the standard compliant data collection mode, such as data identifying the communication session, the user's client device 102, agent's client device, the type of sensitive data to be collected, etc. The API command receiving module 202 receives the API command and notifies the other modules of the standard compliant data collection system 110 to initiate the standard compliant data collection mode.

The API command may be an API command defined by an API provided by the standard compliant data collection system 110 and/or cloud-based communication platform 108 for communicating with and invoking the functionality of the standard compliant collection system 110. For example, the API may define a set of API commands that the online service 106 may use to communicate with the standard compliant data collection system 110, as well as the format of each API command and the functionality it provides. The format of an API commands may include the command term to invoke the API command, the types of data to be included in the API command, the order in which the data is to be included in the API command, and/or the type of data that is returned by the API command. The API may also list a description of the functionality of each listed command.

Software developers of the online service 106 may use the API provided by the standard compliant data collection system 110 to include API commands within the source code of their software applications to invoke the functionality of the standard compliant data collection system 110. For example, an API command to invoke the standard compliant data collection mode may be embedded within the source code such that the API command is executed in response to occurrence of specified conditions or events, such as when a user is prompted to provide sensitive data. Accordingly, the software application will transmit the aforementioned API command upon occurrence of the specified conditions or events.

In response to the API command receiving module 202 receiving an API command from an online service 106 to initiate a standard compliant data collection mode, the secure connection creation module 204 establishes a secure connection between the standard compliant data collection system 110 and the client device 102 of the user that will be providing the sensitive data. The secure connection may be secure in the sense that the secure connection is standard compliant to protect the security of the sensitive data to be shared.

Communication within the communication session is then routed between the standard compliant data collection system 110 and the client device 102 using the secure connection. While the communication session is engaged in the standard compliant data collection mode, the user may provide their sensitive data directly to the standard compliant data collection system 110, where it is collected and stored in a standard-compliant manner. During this period of time, an agent of the online service 106 that was engaged in a communication session with the user may be placed on hold and/or the communication session between the user and agent may be terminated. As a result, the agent is not able to hear the sensitive data provided by the user to the standard compliant data collection system 110.

The standard compliant data collection module 206 facilitates collection of the sensitive data from the user in a standard-compliant manner. For example, the standard compliant data collection module 206 may provide an Interactive Voice Response (IVR) system to prompt and collect the sensitive data from the user. The standard compliant data storage module 208 may also store the sensitive data in the data storage 212 in a standard-compliant manner. The online service 106 may access and/or otherwise use the sensitive data as needed using API commands provided by the standard compliant data collection module 206. The API commands may provide specified functionality to the online service 106 as allowed to comply with mandated standards. For example, the API commands may allow an online service 106 to perform a transaction with a financial institution by causing transmission of the sensitive data to the financial institution, while also restricting visibility to the contents of the sensitive data from the online service 106.

Once the user has successfully provided their sensitive data to the standard compliant data collection module 206, the termination module 210 ends the standard compliant data collection mode. For example, the termination module 210 terminates the secure connection between the client device 102 of the user and the standard compliant data collection system 110. Communication within the communication session is then routed between the client device 102 of the user and the client device 104 of an agent of the online service 106. For example, the hold placed on the client device 104 of the agent is ended and/or a new communication session is established between the client device 102 of the user and the client device 104 of the agent.

Figure 3:
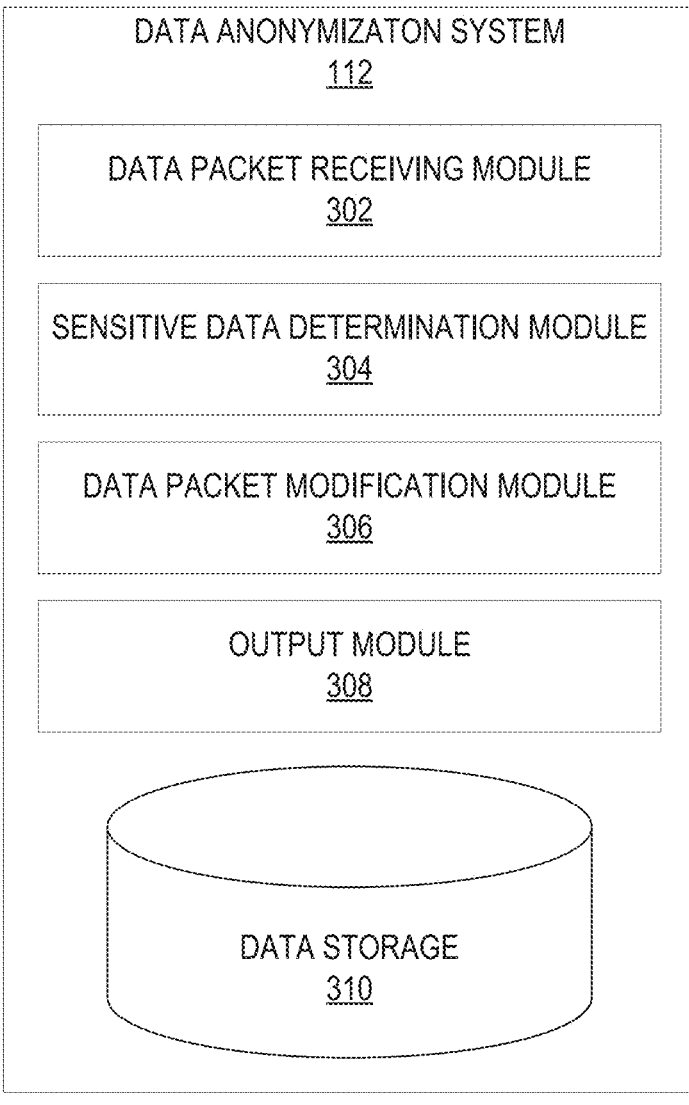
FIG. 3 is a block diagram of the data anonymization system, according to some example embodiments.

FIG. 3 is a block diagram of the data anonymization system 112, according to some example embodiments. To avoid obscuring the inventive subject matter with unnecessary detail, various functional components (e.g., modules) that are not germane to conveying an understanding of the inventive subject matter have been omitted from FIG. 3. However, a skilled artisan will readily recognize that various additional functional components may be supported by the data anonymization system 112 to facilitate additional functionality that is not specifically described herein. Furthermore, the various functional components depicted in FIG. 3 may reside on a single computing device or may be distributed across several computing devices in various arrangements such as those used in cloud-based architectures.

As shown, the data anonymization system 112 includes a data packet receiving module 302, a sensitive data determination module 304, a data packet modification module 306, an output module 308 and a data storage 310.

The data packet receiving module 302 receives data packets transmitted as part of a communication session. The data packets include communications transmitted from a user to an agent or vice versa during a communication session. Accordingly, the data packets may include audio data, text data, video data, etc.

The sensitive data determination module 304 analyzes the data packets to determine whether the data packets include sensitive data, such as digits in a credit card, social security number, etc. In the event the sensitive data determination module 304 determines that a data packet does include sensitive data, the data packet modification module 306 modifies the data packet to replace the sensitive data with default replacement data. The default replacement data provides an indication that the sensitive data was entered, however does not provide an indication as to what the sensitive data is. For example, the default replacement data may be a star symbol used to replace an entered character, such as a numerical digit or letter. As another example, the default replacement data may be a tone used to replace a tone of a user entering their credit card using a telephone (e.g., the default replacement tone is played by a speaker in place of the tone associated with the credit card number). Modifying the data packet result in a modified data packet, which the output module 308 transmits to the intended destination of the data packet within the communication session. As a result, an agent is made aware that the user has entered a value (e.g., number, character, etc.) but cannot discern what specific value was entered.

Figure 4:
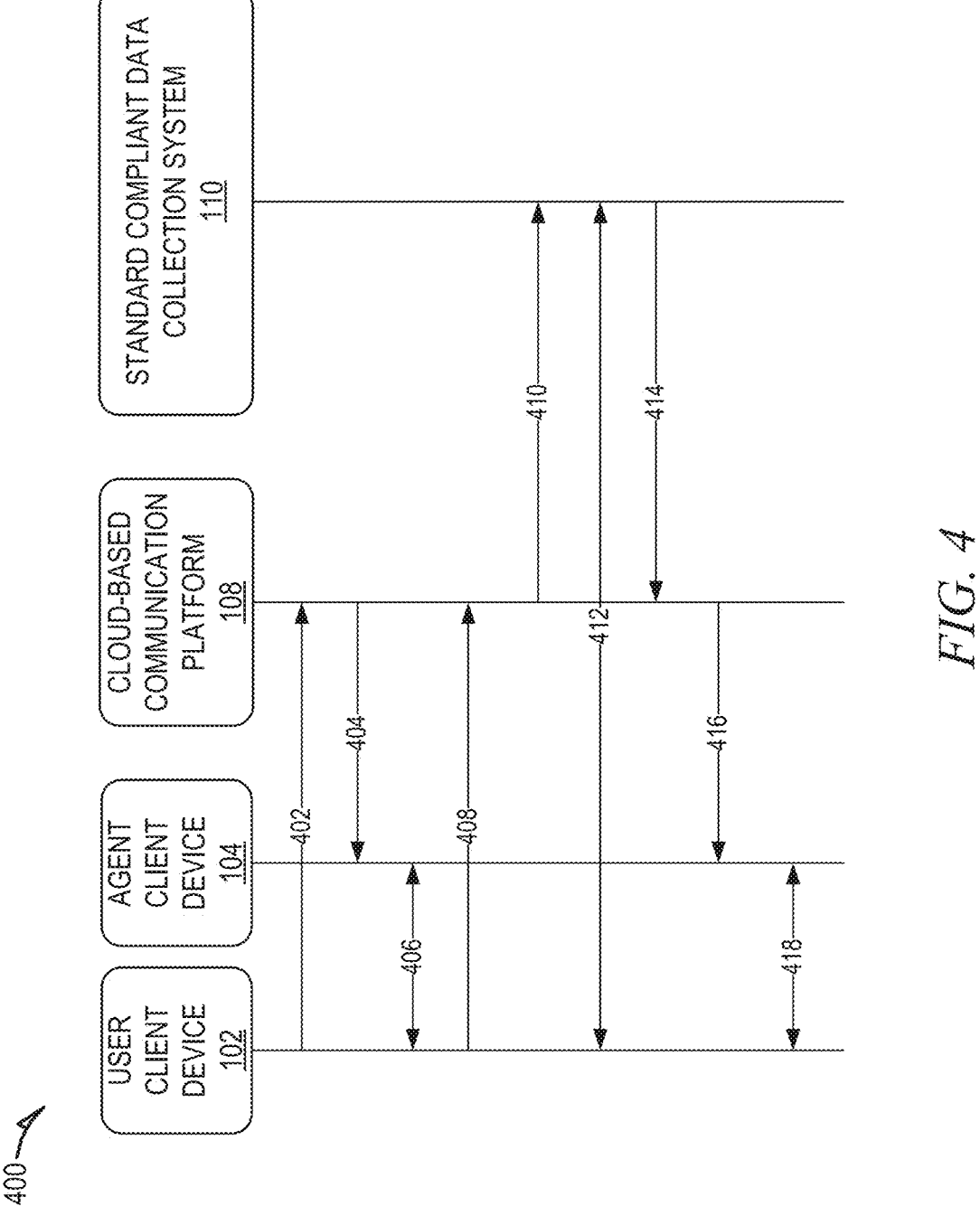
FIG. 4 shows communications in a system for providing standard compliant data collection, according to some example embodiments.

FIG. 4 shows communications in a system 400 for providing standard compliant data collection, according to some example embodiments. As shown, the system 400 includes a user client device 102, an agent client device 104, a cloud-based communication platform 108, and a standard compliant data collection system 110. In the shown system 400, the cloud-based communication platform 108 may facilitate communication functionality, such as a call center, for an online service 106 (not shown). For example, the cloud-based communication platform 108 may provide contact information, such as a phone number, that the online service 106 may provide to their users to contact the call center to communicate with an agent of the online service 106. As another example, the cloud-based communication platform 108 may provide an API, which the online service 106 may embed within their software applications, which allows users to initiate communication (e.g., phone call, message, etc.) with an agent of the online service 106.

As shown, the user client device 102 transmits a communication 402 to the cloud-based communication platform 108 to initiate communication with an agent of an online service 106. For example, the communication 402 may be the result of the user of the user client device 102 dialing a phone number, sending a message to a phone number and/or using functionality provided in a client-side application of the online service 106.

Upon receiving the communication 402, the cloud-based communication platform 108 transmits a communication 404 to the agent client device 104 to initiate a communication session 406 with the user client device 102. Once the communication session 406 is established between the user client device 102 and the agent client device 104, the user may begin communicating with an agent of the online service 106. The agent may be a human agent or an automated agent, such as provided using an IVR system.

During the communication session 406 a user may be prompted to provide sensitive data to the agent, such as credit card information, personal identifiers, patient information, etc. Certain industries, such as the Payment Card Industry (PCI), mandate that a set of standards be followed when collecting, storing, processing, and/or transmitting sensitive data (e.g., credit card data, medical patient data, etc.). The cloud-based communication platform 108 provides a standard compliant data collection system 110 that provides standard compliant data collection to users of the cloud-based communication platform 108. For example, the standard compliant data collection system 110 provides a standard compliant data collection mode in relation to communication sessions when sensitive data is to be collected.

As show, the user client device 102 transmits an indication 408 to the cloud-based communication platform 108 that the user is to provide sensitive data during the communication session 406. The indication 408 may be the result of a user proving an input authorizing collection of the sensitive data, such as by selecting a physical button, user interface element, providing a verbal command, etc. Alternatively, in some embodiments, the indication 408 may be transmitted by the agent client device 104 rather that the user client device 102.

The indication 408 may be transmitted from an application of the online service 106 that is executing on the user client device 102 and/or the agent client device 104. For example, the application may include an API provided by the cloud-based communication platform 108 and/or standard compliant data collection system 110 to invoke the functionality of the standard compliant data collection system 110.

The indication 408 is received by the cloud-based communication platform 108, which in turn transmits an API command 410 to the standard compliant data collection system 110 to initiate a standard compliant data collection mode in relation to the communication session 406. The API command 410 may include data identifying the communication session 406, user client device 102, agent client device 104, and/or the type of sensitive data to be collected.

In response to receiving the API command 410, the standard compliant data collection system 110 establishes a secure connection 412 between the user client device 102 and the standard compliant data collection system 110. The user's sensitive data may be collected via the secure connection 412 in a standard compliant manner. During this time, the agent client device 104 may be placed on a hold and/or the communication session 406 between the user client device 102 and the agent client device 104 may be terminated. As a result, the user's sensitive data is protected from the agent, which is not a party to the communication between the user and the standard compliant data collection system 110.

The standard compliant data collection system 110 transmits a notification 414 to the cloud-based communication platform 108 when the user's sensitive data has been successfully collected by the standard compliant data collection system 110. Accordingly, the secure connection 412 between the user client device 102 and the standard compliant data collection system 110 may be terminated. The cloud-based communication platform 108 may communicate 416 with the agent client device 104 to establish a communications session 418 between the user client device 102 and the agent client device 104. For example, the cloud-based communication platform 108 may end the hold placed on the agent client device 104 and/or establish a new communication session 418 between the user client device 102 and the agent client device 104.

Figure 5:
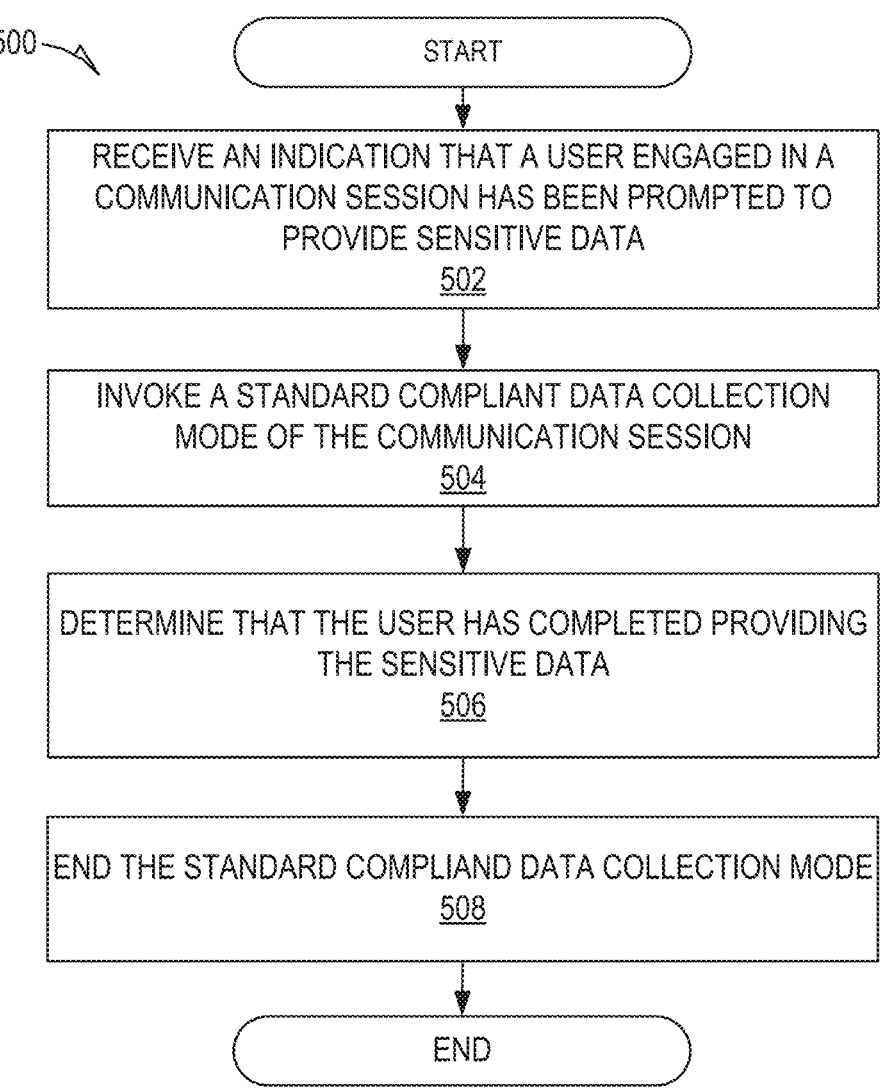
FIG. 5 is a flowchart showing an example method of providing standard compliant data collection, according to some example embodiments.

FIG. 5 is a flowchart showing an example method 500 of providing standard compliant data collection, according to some example embodiments. The method 500 may be embodied in computer readable instructions for execution by one or more processors such that the operations of the method 500 may be performed in part or in whole by the cloud-based communication platform 108; accordingly, the method 500 is described below by way of example with reference thereto. However, it shall be appreciated that at least some of the operations of the method 500 may be deployed on various other hardware configurations and the method 500 is not intended to be limited to the cloud-based communication platform 108. For example, the method 500 may be performed in part or in whole by the cloud-based communication platform 108 and/or the standard compliant data collection system 110.

At operation 502, the cloud-based communication platform 108 receives an indication that a user engaged in a communication session has been prompted to provide sensitive data. The indication may be the result of a user using their client device 102 to provide an input authorizing collection of the sensitive data, such as by selecting a physical button, user interface element, providing a verbal command, etc. Alternatively, in some embodiments, the indication may be transmitted as a result of an agent using their client device 104 to provide an input indicating that sensitive data of the user needs to be collected.

At operation 504, the cloud-based communication platform 108 invokes the standard compliant data collection mode for the communication session. For example, the cloud-based communication platform 108 may transmit a command to the standard compliant data collection system 110 to initiate a standard compliant data collection mode in relation to the communication session. The command may include data identifying the communication session, user's client device 102, agent's client device 104, and/or the type of sensitive data to be collected during the standard compliant data collection mode.

At operation 506, the cloud-based communication platform 108 determines that the user has completed providing the sensitive data. For example, the cloud-based communication platform 108 may receive a notification from the standard compliant data collection system 110 indicating the user's sensitive data has been successfully collected.

At operation 508, the cloud-based communication platform 108 ends the standard compliant data collection mode. For example, the cloud-based communication platform 108 may reestablish the communication session between the client device 102 of the user and the client device 104 of the agent. This may include removing a hold placed on the client device 104 of the agent and/or establishing a new communication session between the client device 102 of the user and the client device 104 of the agent.

FIG. 6 is a flowchart showing an example method 600 of invoking a standard compliant data collection mode, according to some example embodiments. The method 600 may be embodied in computer readable instructions for execution by one or more processors such that the operations of the method 600 may be performed in part or in whole by the standard compliant data collection system 110; accordingly, the method 600 is described below by way of example with reference thereto. However, it shall be appreciated that at least some of the operations of the method 600 may be deployed on various other hardware configurations and the method 600 is not intended to be limited to the standard compliant data collection system 110. For example, the method 600 may be performed in part or in whole by the cloud-based communication platform 108 and/or the standard compliant data collection system 110.

At operation 602, the API command receiving module 202 receives an API command to invoke a standard compliant data collection mode. The API command may be received from a client device 102 of a user, client device 104 of an agent, the cloud-based communication platform 108 or the online service 106. The API command may include data used to initiate the standard compliant data collection mode, such as data identifying the communication session, the user's client device 102, agent's client device 104, the type of sensitive data to be collected, etc. The API command receiving module 202 receives the API command and notifies the other modules of the standard compliant data collection system 110 to initiate the standard compliant data collection mode.

The API command may be an API command defined by an API provided by the standard compliant data collection system 110 and/or cloud-based communication platform 108 for communicating with and invoking the functionality of the standard compliant collection system 110. For example, the API may define a set of API commands that the online service 106 may use to communicate with the standard compliant data collection system 110, as well as the format of each API command and the functionality it provides. The format of an API commands may include the command term to invoke the API command, the types of data to be included in the API command, the order in which the data is to be included in the API command, and/or the type of data that is returned by the API command. The API may also list a description of the functionality of each listed command.

Software developers of the online service 106 may use the API provided by the standard compliant data collection system 110 to include API commands within the source code of their software applications to invoke the functionality of the standard compliant data collection system 110 within their software applications. For example, an API command to invoke the standard compliant data collection mode may be embedded within the source code such that the API command is executed in response to specified conditions or events, such as when a user is prompted to provide sensitive data. Accordingly, the software application will transmit in the aforementioned API command upon occurrence of the specified conditions or events.

At operation 604, the secure connection creation module 204 establishes a secure connection between the client device 102 of the user and the standard compliant data collection system 110. The secure connection may be secure in the sense that the secure connection is standard compliant to protect the security of the sensitive data to be shared.

Communication within the communication session is then routed between the standard compliant data collection system 110 and the client device 102 using the secure connection. While the communication session is engaged in the standard compliant data collection mode, the user may provide their sensitive data directly to the standard compliant data collection system 110, where it is collected and stored in a standard-compliant manner. During this period of time, an agent of the online service 106 that was engaged in a communication session with the user may be placed on hold and/or the initial communication session between the user and agent may be terminated. As a result, the agent is not able to hear the sensitive data provided by the user to the standard compliant data collection system 110.

At operation 606, the standard compliant data collection module 206 collects sensitive data from the user via the secure connection. The standard compliant data collection module 206 facilitates collection of the sensitive data from the user in a standard-compliant manner. For example, the standard compliant data collection module 206 may provide an Interactive Voice Response (IVR) system to prompt and collect the sensitive data from the user. The standard compliant data storage module 208 may also store the sensitive data in the data storage 212 in a standard-compliant manner. The online service 106 may access and/or otherwise use the sensitive data as needed using API provided by the standard compliant data collection module 206. The API commands may provide limited functionality to the online service 106 to provide standard compliance. For example, the API commands may allow an online service 106 to perform a transaction with a financial institution, without providing the online service 106 with visibility to the contents of the sensitive data, such as the user's credit card information.

At operation 608, the standard compliant data storage module 208 stores the collected sensitive data. For example, the standard compliant data storage module 208 may store the sensitive data in the data storage 212 in a standard-compliant manner. Operation 608 is optional, and thus in some embodiments, the collected sensitive data is not stored.

In embodiments in which the sensitive data is stored by the standard compliant data storage module 208, and authorized entity may access and/or otherwise use the sensitive data as needed using API provided by the standard compliant data collection module 206. For example, the online service 106 may use the API commands provided by the standard compliant data collection system 110 to access the stored data. The API commands may include limited functionality to the online service 106 as required to meet standard compliance. For example, the API commands may allow an online service 106 to perform a transaction with a financial institution, while restricting the online service 106 from viewing the contents of the sensitive data, such as the user's credit card information.

At operation 610, the termination module 210 terminates the standard compliant data collection mode. For example, the termination module 210 terminates the secure connection between the client device 102 of the user and the standard compliant data collection system 110. Communication within the communication session is then routed between the client device 102 of the user and the client device 104 of an agent of the online service 106. For example, a hold placed on the client device 104 of the agent may be removed and/or a new communication session may be established between the client device 102 of the user and the client device 104 of the agent.

Software Architecture

Figure 7:
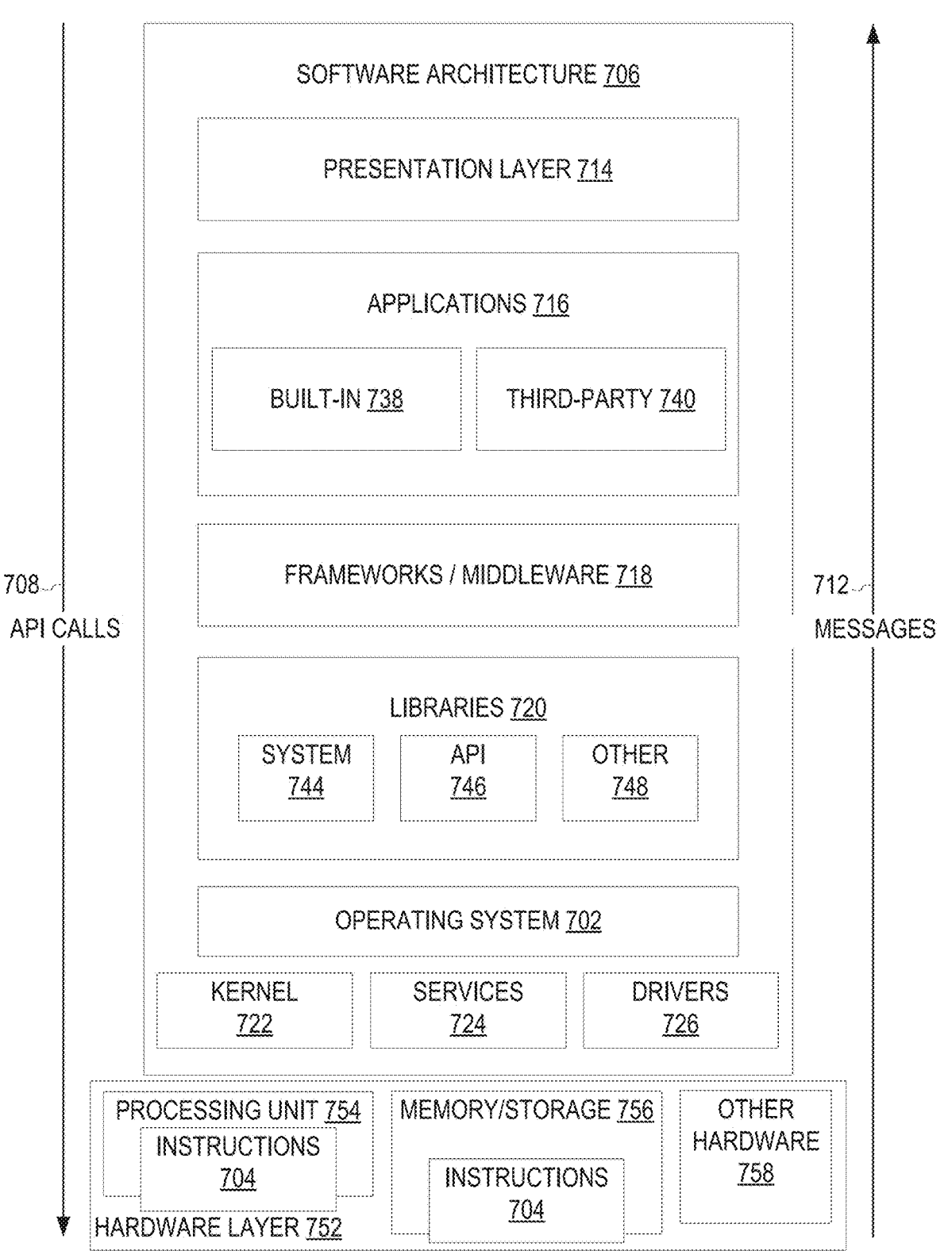
FIG. 7 is a block diagram illustrating components of a machine, according to some example embodiments, able to read instructions from a machine-readable medium (e.g., a machine-readable storage medium) and perform any one or more of the methodologies discussed herein.

FIG. 7 is a block diagram illustrating an example software architecture 706, which may be used in conjunction with various hardware architectures herein described. FIG. 7 is a non-limiting example of a software architecture 706 and it will be appreciated that many other architectures may be implemented to facilitate the functionality described herein. The software architecture 706 may execute on hardware such as machine 800 of FIG. 8 that includes, among other things, processors 804, memory 814, and (input/output) I/O components 818. A representative hardware layer 752 is illustrated and can represent, for example, the machine 800 of FIG. 8. The representative hardware layer 752 includes a processing unit 754 having associated executable instructions 704. Executable instructions 704 represent the executable instructions of the software architecture 706, including implementation of the methods, components, and so forth described herein. The hardware layer 752 also includes memory and/or storage modules 756, which also have executable instructions 704. The hardware layer 752 may also comprise other hardware 758.

In the example architecture of FIG. 7, the software architecture 706 may be conceptualized as a stack of layers where each layer provides particular functionality. For example, the software architecture 706 may include layers such as an operating system 702, libraries 720, frameworks/middleware 718, applications 716, and a presentation layer 714. Operationally, the applications 716 and/or other components within the layers may invoke application programming interface (API) calls 708 through the software stack and receive a response such as messages 712 in response to the API calls 708. The layers illustrated are representative in nature and not all software architectures have all layers. For example, some mobile or special purpose operating systems may not provide a frameworks/middleware 718, while others may provide such a layer. Other software architectures may include additional or different layers.

The operating system 702 may manage hardware resources and provide common services. The operating system 702 may include, for example, a kernel 722, services 724, and drivers 726. The kernel 722 may act as an abstraction layer between the hardware and the other software layers. For example, the kernel 722 may be responsible for memory management, processor management (e.g., scheduling), component management, networking, security settings, and so on. The services 724 may provide other common services for the other software layers. The drivers 726 are responsible for controlling or interfacing with the underlying hardware. For instance, the drivers 726 include display drivers, camera drivers, Bluetooth® drivers, flash memory drivers, serial communication drivers (e.g., Universal Serial Bus (USB) drivers), Wi-Fi® drivers, audio drivers, power management drivers, and so forth, depending on the hardware configuration.

The libraries 720 provide a common infrastructure that is used by the applications 716 and/or other components and/or layers. The libraries 720 provide functionality that allows other software components to perform tasks in an easier fashion than to interface directly with the underlying operating system 702 functionality (e.g., kernel 722, services 724, and/or drivers 726). The libraries 720 may include system libraries 744 (e.g., C standard library) that may provide functions such as memory allocation functions, string manipulation functions, mathematical functions, and the like. In addition, the libraries 720 may include API libraries 746 such as media libraries (e.g., libraries to support presentation and manipulation of various media format such as MPEG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 720 may also include a wide variety of other libraries 748 to provide many other APIs to the applications 716 and other software components/modules.

The frameworks/middleware 718 (also sometimes referred to as middleware) provide a higher-level common infrastructure that may be used by the applications 716 and/or other software components/modules. For example, the frameworks/middleware 718 may provide various graphical user interface (GUI) functions, high-level resource management, high-level location services, and so forth. The frameworks/middleware 718 may provide a broad spectrum of other APIs that may be used by the applications 716 and/or other software components/modules, some of which may be specific to a particular operating system 702 or platform.

The applications 716 include built-in applications 738 and/or third-party applications 740. Examples of representative built-in applications 738 may include, but are not limited to, a contacts application, a browser application, a book reader application, a location application, a media application, a messaging application, and/or a game application. Third-party applications 740 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 740 may invoke the API calls 708 provided by the mobile operating system (such as operating system 702) to facilitate functionality described herein.

The applications 716 may use built in operating system functions (e.g., kernel 722, services 724, and/or drivers 726), libraries 720, and frameworks/middleware 718 to create UIs to interact with users of the system. Alternatively, or additionally, in some systems, interactions with a user may occur through a presentation layer, such as presentation layer 714. In these systems, the application/component "logic" can be separated from the aspects of the application/component that interact with a user.

FIG. 8 is a block diagram illustrating components of a machine 800, according to some example embodiments, able to read instructions 704 from a machine-readable medium (e.g., a machine-readable storage medium) and perform any one or more of the methodologies discussed herein. Specifically, FIG. 8 shows a diagrammatic representation of the machine 800 in the example form of a computer system, within which instructions 810 (e.g., software, a program, an application, an applet, an app, or other executable code) for causing the machine 800 to perform any one or more of the methodologies discussed herein may be executed. As such, the instructions 810 may be used to implement modules or components described herein. The instructions 810 transform the general, non-programmed machine 800 into a particular machine 800 programmed to carry out the described and illustrated functions in the manner described. In alternative embodiments, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a PC, a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine 800 capable of executing the instructions 810, sequentially or otherwise, that specify actions to be taken by machine 800. Further, while only a single machine 800 is illustrated, the term "machine" shall also be taken to include a collection of machines that individually or jointly execute the instructions 810 to perform any one or more of the methodologies discussed herein.

The machine 800 may include processors 804, memory/storage 806, and I/O components 818, which may be configured to communicate with each other such as via a bus 802. The memory/storage 806 may include a memory 814, such as a main memory, or other memory storage, and a storage unit 816, both accessible to the processors 804 such as via the bus 802. The storage unit 816 and memory 814 store the instructions 810 embodying any one or more of the methodologies or functions described herein. The instructions 810 may also reside, completely or partially, within the memory 814, within the storage unit 816, within at least one of the processors 804 (e.g., within the processor's cache memory), or any suitable combination thereof, during execution thereof by the machine 800. Accordingly, the memory 814, the storage unit 816, and the memory of processors 804 are examples of machine-readable media.

The I/O components 818 may include a wide variety of components to receive input, provide output, produce output, transmit information, exchange information, capture measurements, and so on. The specific I/O components 818 that are included in a particular machine 800 will depend on the type of machine. For example, portable machines such as mobile phones will likely include a touch input device or other such input mechanisms, while a headless server machine will likely not include such a touch input device. It will be appreciated that the I/O components 818 may include many other components that are not shown in FIG. 8. The I/O components 818 are grouped according to functionality merely for simplifying the following discussion and the grouping is in no way limiting. In various example embodiments, the I/O components 818 may include output components 826 and input components 828. The output components 826 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 828 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 818 may include biometric components 830, motion components 834, environmental components 836, or position components 838 among a wide array of other components. For example, the biometric components 830 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 834 may include acceleration sensor components (e.g., accelerometer), gravitation sensor components, rotation sensor components (e.g., gyroscope), and so forth. The environmental components 836 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment. The position components 838 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 818 may include communication components 840 operable to couple the machine 800 to a network 832 or devices 820 via coupling 824 and coupling 822, respectively. For example, the communication components 840 may include a network interface component or other suitable device to interface with the network 832. In further examples, communication components 840 may include wired communication components, wireless communication components, cellular communication components, near field communication (NFC) components, Bluetooth® components (e.g., Bluetooth® Low Energy), Wi-Fi® components, and other communication components to provide communication via other modalities. The devices 820 may be another machine or any of a wide variety of peripheral devices (e.g., a peripheral device coupled via a USB).

Moreover, the communication components 840 may detect identifiers or include components operable to detect identifiers. For example, the communication components 840 may include radio frequency identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 840 such as location via Internet Protocol (IP) geo-location, location via Wi-Fi® signal triangulation, location via detecting a NFC beacon signal that may indicate a particular location, and so forth.

Glossary

"CARRIER SIGNAL" in this context refers to any intangible medium that is capable of storing, encoding, or carrying instructions 810 for execution by the machine 800, and includes digital or analog communications signals or other intangible medium to facilitate communication of such instructions 810. Instructions 810 may be transmitted or received over the network 832 using a transmission medium via a network interface device and using any one of a number of well-known transfer protocols.

"CLIENT DEVICE" in this context refers to any machine 800 that interfaces to a communications network 832 to obtain resources from one or more server systems or other client devices 102, 104. A client device 102, 104 may be, but is not limited to, mobile phones, desktop computers, laptops, PDAs, smart phones, tablets, ultra books, netbooks, laptops, multi-processor systems, microprocessor-based or programmable consumer electronics, game consoles, STBs, or any other communication device that a user may use to access a network 832.

"COMMUNICATIONS NETWORK" in this context refers to one or more portions of a network 832 that may be an ad hoc network, an intranet, an extranet, a virtual private network (VPN), a LAN, a wireless LAN (WLAN), a WAN, a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network 832 or a portion of a network 832 may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device or other tangible media able to store instructions 810 and data temporarily or permanently and may include, but is not be limited to, random-access memory (RAM), read-only memory (ROM), buffer memory, flash memory, optical media, magnetic media, cache memory, other types of storage (e.g., erasable programmable read-only memory (EEPROM)), and/or any suitable combination thereof. The term "machine-readable medium" should be taken to include a single medium or multiple media (e.g., a centralized or distributed database, or associated caches and servers) able to store instructions 810. The term "machine-readable medium" shall also be taken to include any medium, or combination of multiple media, that is capable of storing instructions 810 (e.g., code) for execution by a machine 800, such that the instructions 810, when executed by one or more processors 804 of the machine 800, cause the machine 800 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors 804) may be configured by software (e.g., an application 716 or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor 804 or other programmable processor 804. Once configured by such software, hardware components become specific machines 800 (or specific components of a machine 800) uniquely tailored to perform the configured functions and are no longer general-purpose processors 804. It will be appreciated that the decision to implement a hardware component mechanically, in dedicated and perma-nently configured circuitry, or in temporarily configured circuitry (e.g., configured by software), may be driven by cost and time considerations. Accordingly, the phrase "hard-ware component" (or "hardware-implemented component") should be understood to encompass a tangible entity, be that an entity that is physically constructed, permanently con-figured (e.g., hardwired), or temporarily configured (e.g., programmed) to operate in a certain manner or to perform certain operations described herein. Considering embodi-ments in which hardware components are temporarily con-figured (e.g., programmed), each of the hardware compo-nents need not be configured or instantiated at any one instance in time. For example, where a hardware component comprises a general-purpose processor 804 configured by software to become a special-purpose processor, the general-purpose processor 804 may be configured as respectively different special-purpose processors (e.g., comprising dif-ferent hardware components) at different times. Software accordingly configures a particular processor or processors 804, for example, to constitute a particular hardware com-ponent at one instance of time and to constitute a different hardware component at a different instance of time. Hard-ware components can provide information to, and receive information from, other hardware components. Accordingly, the described hardware components may be regarded as being communicatively coupled. Where multiple hardware components exist contemporaneously, communications may be achieved through signal transmission (e.g., over appro-priate circuits and buses 802) between or among two or more of the hardware components. In embodiments in which multiple hardware components are configured or instanti-ated at different times, communications between such hard-ware components may be achieved, for example, through the storage and retrieval of information in memory structures to which the multiple hardware components have access. For example, one hardware component may perform an opera-tion and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors 804 that are temporarily configured (e.g., by software) or permanently configured to perform the relevant operations. Whether temporarily or permanently configured, such processors 804 may constitute processor-implemented components that operate to perform one or more operations or functions described herein. As used herein, "processor-implemented component" refers to a hardware component implemented using one or more processors 804. Similarly, the methods described herein may be at least partially processor-imple-mented, with a particular processor or processors 804 being an example of hardware. For example, at least some of the operations of a method may be performed by one or more processors 804 or processor-implemented components. Moreover, the one or more processors 804 may also operate to support performance of the relevant operations in a "cloud computing" environment or as a "software as a service" (SaaS). For example, at least some of the operations may be performed by a group of computers (as examples of machines 800 including processors 804), with these opera-tions being accessible via a network 832 (e.g., the Internet) and via one or more appropriate interfaces (e.g., an API). The performance of certain of the operations may be dis-tributed among the processors 804, not only residing within a single machine 800, but deployed across a number of machines 800. In some example embodiments, the proces-sors 804 or processor-implemented components may be located in a single geographic location (e.g., within a home environment, an office environment, or a server farm). In other example embodiments, the processors 804 or proces-sor-implemented components may be distributed across a number of geographic locations.

"PROCESSOR" in this context refers to any circuit or virtual circuit (a physical circuit emulated by logic executing on an actual processor 804) that manipulates data values according to control signals (e.g., "commands," "op codes," "machine code," etc.) and which produces corresponding output signals that are applied to operate a machine 800. A processor 804 may be, for example, a central processing unit (CPU), a reduced instruction set computing (RISC) proces-sor, a complex instruction set computing (CISC) processor, a graphics processing unit (GPU), a digital signal processor (DSP), an ASIC, a radio-frequency integrated circuit (RFIC) or any combination thereof. A processor 804 may further be a multi-core processor having two or more independent processors 804 (sometimes referred to as "cores") that may execute instructions 810 contemporaneously.

What is claimed is:

1. A method performed by a communications platform, the method comprising:

establishing a communication session between a user device and an agent device;

receiving an authorization to collect sensitive data from the user device;

in response to the receiving of the authorization, suspending the communication session between the user device and the agent device, invoking, via an application programming interface (API) command of a standard compliant data col-lection system, a standard compliant data collection mode that causes communications within the com-munication session to be temporarily routed to the standard compliant data collection system, and causes the sensitive data to be collected during the standard compliant data collection mode based on configuration data included in the API command, wherein the configuration data defines parameters for customizing operations of the standard compliant data collection system including one or more param-eters defining a customizable message flow for col-lecting the sensitive data, and one or more param-eters for controlling presentation of prompts during the message flow, receiving, from the standard compliant data collection system, a notification, wherein the notification comprises information that the sensitive data of the user device has been collected; and in response to receiving the notification, ending the standard compliant data collection mode, wherein the ending the standard compliant data collection mode further comprises terminating the secure connection with the standard compliant data collection system, and re-establishing the communication session between the user device and the agent device.

2. The method of claim 1, wherein the user device is connected to a communication network by utilizing functionality of an online service via a third-party application for accessing the API of the standard compliant data collection system.

3. The method of claim 1, further comprises defining error handling during the standard compliant data collection mode, including transmitting a notification to the user device and prompting for a correction of the sensitive data based on detection of an error in previously collected sensitive data.

4. The method of claim 1, wherein the communication session includes a video call between the agent device and the user device.

5. The method of claim 1, further comprising:

transmitting a record of the communication session to a data anonymization system, wherein the data anonymization system modifies data transmitted as part of the communication session to replace the sensitive data with default data.

6. The method of claim 1, wherein the standard compliant data collection system configures the sensitive data in a pre-defined way defined by the configuration data.

7. The method of claim 1, wherein the configuration data is defined by language based on geographical location provided by the user device.

8. The method of claim 1, wherein the configuration data includes resource identifiers associated with an event trigger.

9. The method of claim 8, further comprises:

transmitting a notification corresponding with the event trigger and data configured by the configuration data to the agent device.

10. A system comprising:

one or more computer processors; and one or more computer memories storing a set of instructions that, when executed by the one or more computer processors, cause the one or more computer processors to perform operations, the operations comprising:

establishing a communication session between a user device and an agent device;

receiving an authorization to collect sensitive data from the user device;

in response to the receiving of the authorization, suspending the communication session between the user device and the agent device, invoking, via an application programming interface (API) command of a standard compliant data collection system, a standard compliant data collection mode that causes communications within the communication session to be temporarily routed to the standard compliant data collection system, and causes the sensitive data to be collected during the standard compliant data collection mode based on configuration data included in the API command, wherein the configuration data defines parameters for customizing operations of the standard compliant data collection system including one or more parameters defining a customizable message flow for collecting the sensitive data, and one or more parameters for controlling presentation of prompts during the message flow, receiving, from the standard compliant data collection system, a notification, wherein the notification comprises information that the sensitive data of the user device has been collected; and in response to receiving the notification, ending the standard compliant data collection mode, wherein the ending the standard compliant data collection mode further comprises terminating the secure connection with the standard compliant data collection system, and re-establishing the communication session between the user device and the agent device.

11. The system of claim 10, wherein the communication session includes an active video call between the agent device and the user device.

12. The system of claim 10, wherein the configuration data is defined by language based on geographical location provided by the user device.

13. The system of claim 10, wherein the configuration data includes resource identifiers associated with an event trigger.

14. A non-transitory computer-readable medium storing instructions that, when executed by one or more computer processors of a system, cause the one or more computer processors to perform operations, the operations comprising:

establishing a communication session between a user device and an agent device;

receiving an authorization to collect sensitive data from the user device;

in response to the receiving of the authorization, suspending the communication session between the user device and the agent device, invoking, via an application programming interface (API) command of a standard compliant data collection system, a standard compliant data collection mode that causes communications within the communication session to be temporarily routed to the standard compliant data collection system, and causes the sensitive data to be collected during the standard compliant data collection mode based on configuration data included in the API command, wherein the configuration data defines parameters for customizing operations of the standard compliant data collection system including one or more parameters defining a customizable message flow for collecting the sensitive data, and one or more parameters for controlling presentation of prompts during the message flow, receiving, from the standard compliant data collection system, a notification, wherein the notification comprises information that the sensitive data of the user device has been collected; and in response to receiving the notification, ending the standard compliant data collection session mode, wherein the ending the standard compliant data collection mode further comprises terminating the secure connection with the user device, and re-establishing the communication session between the user device and the agent device.

15. The non-transitory computer-readable medium of claim 14, wherein the instructions, when executed by the one or more computer processors, cause the one or more computer processors to perform the operations further comprising:

transmitting a record of the communication session to a data anonymization system and causing the data anonymization system to modify data transmitted as part of the communication session to replace the sensitive data with default data.

16. The method of claim 1, wherein the customizing of the performance of the standard compliant data collection system includes defining a message flow, a language, an action, or a trigger that is to be used during the collecting of the sensitive data.

17. The method of claim 1, wherein the one or more parameters for controlling presentation of prompts includes parameters for causing a prompt to be played or a notification to be transmitted in response to an error occurring during the standard compliant data collection mode.

18. The system of claim 10, wherein communications between the user device and the standard compliant data collection system occur via a communication network, the communications being facilitated by an online service through a third-party application configured to access the API of the standard compliant data collection system.

19. The system of claim 10, wherein the set of instructions that, when executed by the one or more computer processors, cause the one or more computer processors to further perform the operations comprising:

transmitting a record of the communication session to a data anonymization system, and causing the data anonymization system, upon receiving the record, to modify data transmitted as part of the communication session by replacing the sensitive data with default data.

20. The system of claim 10, the set of instructions that, when executed by the one or more computer processors, cause the one or more computer processors to further perform the operations comprising:

causing the standard compliant data collection system to configure the sensitive data in a pre-defined way according to the configuration data included in the API command.

\* \* \* \* \*